(12) United States Patent
Gerson

(10) Patent No.: US 8,318,495 B1
(45) Date of Patent: Nov. 27, 2012

(54) HEMATOPOIETIC PROGENITOR CELL GENE TRANSDUCTION

(75) Inventor: Stanton L. Gerson, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 404 days.

(21) Appl. No.: 09/321,655

(22) Filed: May 28, 1999

Related U.S. Application Data

(60) Provisional application No. 60/087,284, filed on May 29, 1998.

(51) Int. Cl.
*C12N 15/63* (2006.01)
*C12N 5/00* (2006.01)
*A61K 48/00* (2006.01)

(52) U.S. Cl. ........................................ 435/455; 435/373
(58) Field of Classification Search ................. 424/93.7, 424/93.21; 435/325, 455, 456, 324, 347, 435/363, 366, 372, 373, 320.1
See application file for complete search history.

(56) References Cited

U.S. PATENT DOCUMENTS

| | | | | |
|---|---|---|---|---|
| 5,486,359 A * | 1/1996 | Caplan et al. | ................. | 424/93.7 |
| 5,591,625 A * | 1/1997 | Gerson et al. | ................. | 435/325 |
| 6,225,119 B1 * | 5/2001 | Qasba et al. | ................. | 435/373 |
| 7,592,174 B2 * | 9/2009 | Sylvester et al. | ............. | 435/325 |
| 2002/0168765 A1 * | 11/2002 | Prockop et al. | ............... | 435/366 |

FOREIGN PATENT DOCUMENTS

WO WO 92/22584 * 12/1992

OTHER PUBLICATIONS

Dang, V.C. et al. Gene therapy and translational cancer research. Clin. Cancer Res. 5:471-474, 1999.*
Eck, S.L. & Wilson, J.M. Gene-based therapy. Goodman & Gilman's The pharmacological basis of therapeutics, Ninth edition, pp. 77-101, 1996.*
Prockop, D.J. Marrow stromal cells as stem cells for nonhematopoietic tissues. Science 276:71-74, 1997.*
Gerson, S.L. Mesenchymal stem cells: No longer second class marrow citizens. Nature Med. 5:262-264, 1999.*
Koc, O.N. et al. Rapid hematopoietic recovery after coinfusion of autologous-blood stem cells and cultureexpanded marrow mesenchymal stem cells in advanced breast cancer patients receiving high-dose chemotherapy. J. Clin. Oncol. 18:307-316, 2000.*
Deisseroth, A.B. Clinical trials involving multidrug resistance transcription units in retroviral vectors. Clin. Cancer. Res. 5:1607-1609, 1999.*
Reese, J.S. et al. Retroviral transduction of a mutant methylguanine DNA methyltransferase gene into human CD34 cells confers resistance to O6-benzylguanine plus 1,3-bis(2-chloroethyl)-1-nitrosourea. Proc. Natl. Acad. Sci. 93:14088-14093, 1996.*
Nolta, J.A et al. Analysis of optimal conditions for retroviral-mediated transduction of primitive human hematopoietic cells. Blood 86:101-110, 1995.*
Wells et al. The presence of an autologous marrow stromal cell layer increases glucocerebrosidase gene transduction of longterm culture initiating cells (LTCICs) from the bone marrow of a patient with Gaucher disease. Gene therapy 2:512-520, 1995.*
Mesenchymal stem cell. Wikipedia, the free encyclopedia, pp. 1-5, 2009.*

* cited by examiner

*Primary Examiner* — Quang Nguyen
(74) *Attorney, Agent, or Firm* — Tarolli, Sundheim, Covell & Tummino LLP

(57) ABSTRACT

Genetically engineered hematopoietic progenitor cells that carry within them genes of interest, particularly for the expression of physiologically or pharmacologically active proteins. The hematopoietic progenitor cells are transduced in the presence of human mesenchymal stem cells which enhance transduction efficiency.

5 Claims, 3 Drawing Sheets

SEQUENCE LISTING

<160> NUMBER OF SEQ ID NOS: 2

<210> SEQ ID NO 1
<211> LENGTH: 23
<212> TYPE: DNA
<213> ORGANISM: Homo sapiens

<400> SEQUENCE: 1
tggtacctca cccttaccga gtc                                       23

<210> SEQ ID NO 2
<211> LENGTH: 27
<212> TYPE: DNA
<213> ORGANISM: Homo sapiens

<400> SEQUENCE: 2
acacctgtct ggtgaacgaa cgactct                                   27

HEMATOPOIETIC PROGENITOR CELL GENE TRANSDUCTION

This application claims priority based on provisional application Ser. No. 60/087,284, filed May 29, 1998.

The present invention relates to the genetic transformation of cells and more particularly to the transformation of hematopoietic stem cells.

BACKGROUND OF THE INVENTION

The introduction of foreign genes into human hematopoietic stem cells has been described (Allay, et al. 1996). Genetic modification of hematopoietic cells using retrovirus-based vectors has resulted in low transduction efficiency. Factors known to increase efficiency of gene transduction into hematopoietic progenitor cells include fibronectin and cytokines as well as attempts to decrease the frequency of non-specific adhesion of retrovirus to target cells which interferes with the transduction process (see e.g. Hanenberg et al. 1997). Bone marrow stromal cells in co-culture with hematopoietic stem cells and retrovirus have been shown to enhance transduction (Moore et al. 1992; Nolta et al. 1995).

Alternative methods to increase transduction efficiency of hematopoietic cells would be advantageous in cases where such reagents are not readily available or would not be suitable.

SUMMARY OF THE INVENTION

The present invention is directed to human hematopoietic stem cells that are genetically engineered to carry within them genes of interest, particularly for the expression of physiologically or pharmacologically active proteins.

In accordance with the present invention, it has been discovered that human mesenchymal stem cells (hMSCs) can be used to enhance the transduction of human hematopoietic progenitor cells for the expression of exogenous gene products. The mesenchymal stem cells can be allogeneic or autologous to the hematopoietic progenitor cells. In a preferred embodiment, the human hematopoietic progenitor cells are CD34+ cells.

Utilizing mesenchymal stem cells as described herein provides a method of enhancing gene transduction with a reagent that may be derived from alternate sources in that either autologous or allogeneic mesenchymal stem cells may be used for the method described herein. The mesenchymal stem cells represent a well characterized cell population which can be prepared in a much more reproducible manner than, for example, the heterogeneous Dexter-like stromal culture. Dexter stroma, in addition to MSCs, contains T and B lymphocytes, macrophages, dendritic cells and endothelial cells.

For purposes of the present invention, the mesenchymal stem cells may be used in the absence or presence of exogenous growth factors or cytokines.

In its principal embodiment, the invention relates to a method of transducing human hematopoietic stem cells to express an incorporated genetic material of interest. Human hematopoietic stem cells are isolated from an individual donor. The isolated hematopoietic progenitor cells are transduced in the presence of human mesenchymal stem cells such that they are able to express exogenous gene products. It is contemplated that the transformed cells and the expression products of the incorporated genetic material can be used alone or in combination with other cells and/or compositions.

In a still further aspect, the transduced human hematopoietic progenitor cells are separated from the human mesenchymal stem cells prior to utilization of the transduced hematopoietic stem cells for their intended purpose.

Accordingly, in one aspect the invention involves a method of modifying human hematopoietic progenitor cells with genetic material of interest in the presence of the mesenchymal stem cells. The transduced hematopoietic stem cells genes may be used to produce the material of interest, for example, a protein or polypeptide, by in vitro expression of the protein which may be useful for specific therapeutic applications or non-therapeutic applications. The genetic material of interest may express, for example, intracellular gene products, signal transduction molecules, cell surface proteins, extracellular gene expression products and hormone receptors.

In another aspect, the hematopoietic stem cells are transduced ex-vivo for subsequent in vivo use, i.e. transduced with a polynucleotide encoding a therapeutic protein and the cells administered to a mammal in need thereof for in vivo expression of a therapeutically effective amount.

Examples of genetic material for transduction into hematopoietic progenitor cells includes the expression of gene products which have a role in hematopoietic cell maintenance, tissue development, remodeling, repair and in vivo production of extracellular gene products.

DETAILED DESCRIPTION OF THE INVENTION

Figure 1A:
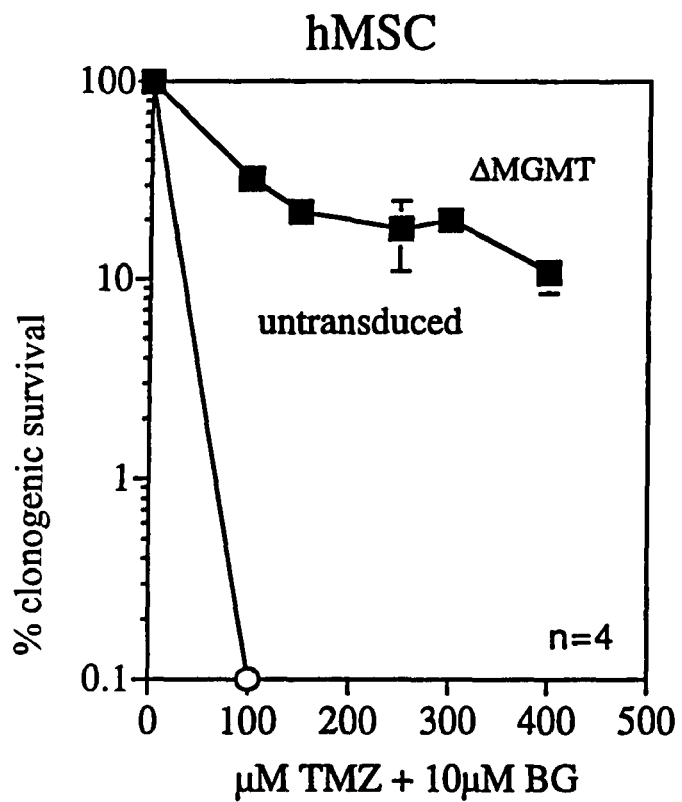
FIG. 1A-1C: Drug resistance in hematopoietic progenitors transduced in the presence of hMSCs. Shown is a comparison of the number of colonies of cells, transduced with ΔMGMT in the presence of hMSCs (FIG. 1A); fibronectin (FN) (FIG. 1B), and Dexter stroma (FIG. 1C) surviving after exposure of the transduced cells to TMZ or BCNU, as compared to untransduced cells under the same conditions. Error bars represent SEM.

The present invention provides a method of transducing hematopoetic progenitor cells comprising contacting the hematopoietic progenitor cells with exogenous genetic material and human mesenchymal stem cells.

In one aspect, the mesenchymal stem cells are autologous to the hematopoietic progenitor cells. In another aspect, the mesenchymal stem cells are allogeneic to the hematopoietic progenitor cells.

In another aspect, the transduced human hematopoietic progenitor cells and the mesenchymal stem cells may be used together. In a still further aspect, the human hematopoietic progenitor cells are separated from the mesenchymal stem cells after the hematopoietic progenitor cells have been transduced. One of skill in the art would be able to ascertain which mode of use would be suitable depending on the purpose for the transduced cells.

Isolated human hematopoietic stem cells have been described, for example, in Tsuksamoto et al., U.S. Pat. No. 5,061,620 (1991) and reviewed in Edgington, *Biotechnology,*

10:1099-1106 (1992) and the references cited therein. These are distinguished from mesenchymal stem cells by their ability to differentiate into myeloid and lymphoid blood cells.

The hematopoietic progenitor cells can be obtained according to known methods, for example, from peripheral blood mononuclear cells or bone marrow. In a preferred embodiment, the human hematopoietic progenitor cells are CD34+ cells. These progenitor hematopoietic cells can be isolated, for example, by positive antibody selection.

Mesenchymal stem cells (MSCs) can be derived from marrow, periosteum, dermis and other tissues of mesodermal origin. The mesenchymal stem cells can be isolated and prepared according to methods known in the art, for example, a process for isolating, purifying, and expanding the marrow-derived mesenchymal stems cells in culture, i.e. in vitro, is described in U.S. Pat. Nos. 5,197,985 and 5,226,914 and PCT Publication No. WO 92/22584 (1992), which are incorporated herein by reference in their entirety, as well as numerous literature references by Caplan and Haynesworth. The stem cells may be isolated from other cells by density gradient fractionation, such as by Percoll gradient fractionation. The human mesenchymal stem cells also can include a cell surface epitope specifically bound by antibodies from hybridoma cell line SH2, deposited with the ATCC under accession number HB10743; antibodies from hybridoma cell line SH3, deposited with the ATCC under accession number HB10744; or antibodies from hybridoma cell line SH4, deposited with the ATCC under accession number HB10745.

The hMSCs can be distinguished from the more complex cellular microenvironment present for example in the marrow stroma ("Dexter stroma"). MSCs are distinct in morphology from Dexter stroma and also lack surface markers for T and B lymphocytes, macrophages and endothelial cells.

The culture conditions such as temperature pH and the like, are those previously used with hematopoietic progenitor cells, and will be apparent to the ordinarily skilled artisan. The transformed hematopoietic progenitor cells are maintained in a medium that stimulates culture expansion but does not stimulate their differentiation.

The cells may be co-cultured in a medium such as supplemented $BGJ_b$ medium or supplemented F-12 Nutrient Mixture. Preferably the medium is a human MSC medium which comprises Dulbecco's Modified Eagles Medium Low Glucose (DMEM-LG) (Life Technologies) supplemented preferably with fetal bovine serum. The composition can also be supplemented with an antibiotic and antimycotic composition.

In one embodiment, the transduction may be effected in the absence of exogenous cytokines.

However, in a more preferred embodiment, in addition to the human mesenchymal stem cells, the hematopoietic stem cells may be transduced in the presence of one or more cytokines. Representative examples of cytokines that may be employed in the present invention include interleukin-1 (IL-1), IL-6, IL-3, stem cell factor (SCF), Flt-3 ligand, leukemia inhibitory factor (LIF), granulocyte-macrophage colony stimulating factor (GM-CSF), c-kit ligand and IL-3-GM-CSF fusion protein.

The mesenchymal stem cells may be irradiated prior to use in order to minimize or eliminate transduction of the mesenchymal stem cells. However, it is also possible to use non-irradiated mesenchymal stem cells, which may result in both transduced mesenchymal stem cells and transduced hematopoietic stem cells. Again, one of skill in the art would be able to judge depending on the purpose of the transduced cells whether it will be necessary to separate the two cell population prior to use. Thus, the transduced hematopoietic progenitor cells may be used alone or together with transduced mesenchymal stem cells.

After modification of the hematopoietic cells, the mixture of hematopoietic and mesenchymal stem cells may be separated to obtain a population of cells largely consisting of the transduced hematopoietic stem cells. This may be accomplished by positive and/or negative selection of transduced hematopoietic cells using antibodies to identify hematopoietic cell surface markers or by culturing out adherent mesenchymal stem cells and recovering a substantially homogenous population of transduced hematopoietic cells from the supernatant.

The hematopoietic stem cells may be genetically modified (transduced or transformed or transfected) by incorporation of genetic material into the cells, for example using recombinant expression vectors.

As used herein "recombinant expression vector" refers to a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The human hematopoietic progenitor cells transduced in the presence of human mesenchymal stem cells thus may have stably integrated a recombinant transcriptional unit into chromosomal DNA or carry the recombinant transcriptional unit as a component of a resident plasmid. Cells may be engineered with a polynucleotide (DNA or RNA) encoding a polypeptide ex vivo, for example. Cells may be engineered by procedures known in the art by use of a retroviral particle containing RNA encoding a polypeptide.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus. Generally regarding retroviral mediated gene transfer, see McLachlin et al. (1990).

The nucleic acid sequence encoding the polypeptide is under the control of a suitable promoter. Suitable promoters which may be employed include, but are not limited to, adenoviral promoters, such as the adenoviral major late promoter; the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters. The promoter also may be the native promoter that controls the gene encoding the polypeptide. These vectors also make it possible to regulate the production of the polypeptide by the engineered progenitor cells. The selection of a suitable promoter will be apparent to those skilled in the art.

The producer cell line generates infectious retroviral vector particles which include the nucleic acid sequence(s) encoding the polypeptides. Such retroviral vector particles then may be employed to transduce the hematopoietic stem cells, either in vitro or in vivo. The transduced hematopoietic stem cells will express the nucleic acid sequence(s) encoding the polypeptide.

It is also possible to use vehicles other than retroviruses to genetically engineer or modify the hematopoietic stem cells. Genetic information of interest can be introduced by means of any virus which can express the new genetic material in such cells. For example, SV40, herpes virus, adenovirus and human papillomavirus can be used for this purpose. Other methods can also be used for introducing cloned eukaryotic DNAs into cultured mammalian cells, for example, the genetic material to be transferred to stem cells may be in the form of viral nucleic acids.

In addition, the expression vectors may contain one or more selectable marker genes to provide a phenotypic trait for selection of transformed cells such as dihydrofolate reductase or neomycin resistance.

The hematopoietic progenitor cells may be transfected through other means known in the art. Such means include, but are not limited to transfection mediated by calcium phosphate or DEAE-dextran; transfection mediated by the polycation Polybrene (Kawai and Nishizawa 1984; Chaney et al. 1986); protoplast fusion (Robert de Saint Vincent et al. 1981). (Schaffner 1980; Rassoulzadegan et al. 1982); electroporation (Neumann et al. 1982; Zimmermann 1982) (Boggs et al. 1986); liposomes (see, e.g. Mannino and Gould-Fogerite (1988)), either through encapsulation of DNA or RNA within liposomes, followed by fusion of the liposomes with the cell membrane or, DNA coated with a synthetic cationic lipid can be introduced into cells by fusion (Feigner et al. (1987); Felgner and Holm 1989; Maurer 1989).

The present invention further makes it possible to genetically engineer human hematopoietic progenitor cells in such a manner that they produce, in vitro, polypeptides, hormones and proteins not normally produced in human hematopoietic progenitor cells in biologically significant amounts or produced in small amounts but in situations in which overproduction would lead to a therapeutic benefit. These products would then be secreted into the surrounding media or purified from the cells. The human hematopoietic progenitor cells formed in this way can serve as continuous short term or long term production systems of the expressed substance.

This technology may be used to produce additional copies of essential genes to allow augmented expression of certain gene products in vivo. These genes can be, for example, hormones, matrix proteins, cell membrane proteins, cytokines, adhesion molecules, detoxification enzymes, "rebuilding" proteins important in tissue repair and drug resistance. The expression of the exogenous genetic material in vivo, is often referred to as "gene therapy." Disease states and procedures for which such treatments have application include genetic disorders and diseases of the blood and immune system. Cell delivery of the transformed cells may be effected using various methods and includes infusion and direct depot injection into periosteal, bone marrow and subcutaneous sites.

In addition, as hereinabove described, the transduced cells may be used for in vitro production of desired protein(s).

The above description of the invention within its scope includes modifications which are apparent to those of skill in the art. The example which follows further illustrates, and is not a limitation of, the scope of the present invention.

EXAMPLE

Human mesenchymal stem cells (hMSCs) were isolated and cultured using a previously reported method (Haynesworth et al., 1992) with modifications. Briefly, 25 ml of heparinized bone marrow was mixed with an equal volume of phosphate-buffered saline (PBS) (Life Technologies, Gaithersburg, Md.) and centrifuged at 900 g for 10 minutes at room temperature. Washed cells were resuspended in PBS to a final density of $4 \times 10^7$ cells/cm$^2$, and a 5 ml aliquot was layered over a 1.073 g/ml Percoll solution (Pharmacia, Piscataway, N.J.) and centrifuged at 900×g for 30 minutes. Mononuclear cells collecting at the interface were recovered, resuspended in human MSC medium, and plated at a density of $3 \times 10^7$ cells per 185 cm$^2$ Nunclon Solo flask (Nunc Inc., Naperville, Ill.). Homogeneity of the culture was determined by uniform expression of the hMSC specific surface protein SH2, 3, and 4. Human MSC medium consisted of Dulbecco's modified Eagles Medium-Low Glucose (DMEM-LG) (Life Technologies) supplemented with 10% fetal bovine serum (FBS) (Biocell Laboratories, Rancho Dominguez, Calif.) which was screened for its ability to support culture expansion of MSCs, and 1% antibiotic-antimycotic solution (Life Technologies). Mesenchymal stem cell cultures were maintained at 37° C. in 5% $CO_2$ in air, with medium changes after 48 hours and every 3-4 days thereafter. When the cultures reached 90% of confluence, the cells were recovered by the addition of a solution containing 0.25% trypsin-EDTA (Life Technologies) and replated at a density of $1 \times 10^6$ cells per 185 cm$^2$ flask as passage 1 cells.

Dexter stroma was obtained by mixing bone marrow with an equal volume of phosphate buffered saline (PBS) containing 2% bovine serum albumin (BSA) (Life Technologies), 0.6% sodium citrate (Sigma, St. Louis, Mo.), and 1% penicillin-streptomycin (Life Technologies), and aliquots were layered over Ficoll-Paque (1.077 gm/ml) (Pharmacia) and centrifuged at 800×g for 20 minutes. The mononuclear cells that collected at the interface were suspended in medium consisting of MyeloCult H5100 (Stem Cell Technologies, Vancouver, BC, Canada) supplemented with 1 µM hydrocortisone (Sigma), plated at a density of $60 \times 10^6$ cells per 185 cm$^2$ flask, and incubated at 33° C. in 5% $CO_2$ in air with media changes after 10 days and then every 7 days thereafter. MyeloCult H5100 is made up of 12.5% FBS, 12.5% horse serum, 0.2 mM i-inositol, 20 mM folic acid, 0.1 mM 2-mercaptoethanol, 2 mM L-glutamine in Alpha MEM. Primary cultures were recovered by trypsinization when the cells reached 90% of confluence and replated at a density of $1 \times 10^6$ cells per 185 cm$^2$ flask as passage 1 cells.

Peripheral blood mononuclear cells were obtained by apheresis from normal donors treated with G-CSF under an Institutional Review Board approved protocol. CD34+ cells were isolated by positive selection using the VarioMacs column (Miltenyi Biotec, Inc. Auburn, Calif.) with a purity of 72%±17.

Flasks containing fibronectin fragment CH-296 (FN) (Takara Biochemicals) were prepared according to the method described by Hanenberg et al. 1997 with modifications. Bacterial (=non-tissue culture-treated) T75 cm$^2$ flasks (Falcon, Franklin Lakes, N.J.) were coated with 17 µg/cm$^2$ of the recombinant *Escherichia coli*-derived FN fragments CH-296 (Takara Shuzo, Otsu, Japan) similarly as described (Hanenberg et al. 1996). A 2.5-mg amount of CH-296 (dry powder) was dissolved in 2.5 ml of sterile distilled water and then diluted in phosphate buffered saline (PBS, GIBCO) to appropriate concentrations. After 2 hours at room temperature, flasks were blocked by adding 1 or 2 ml of 2% bovine serum albumin (BSA; fraction V, protease-free; Boehringer Mannheim, Indianapolis, Ind.) in PBS for at least 30 minutes. Flasks were then washed with 2 or 4 ml of medium to remove unbound CH-296.

CD34+ cells were transduced with MFG-ΔMGMT high titer retroviral supernatant obtained as described in Reese et al. 1996. ΔMGMT encodes a mutant form of $O^{-6}$ alkylguanine DNA alkyltransferase (ΔAGT) and contains a point mutation which renders the protein resistant to the inhibitor $O^6$-benzylguanine (BG). CD34+ cells transduced with ΔMGMT are resistant to the drug combinations BG and 1,3bis(2-chloroethly)-1-nitrosourea (BCNU) (Reese et al. 1996) and BG and temozolomide (TMZ) (Reese et al. 1998). The CD34+ cells were transduced as follows: pMFG-wt-MGMT or pMFG-ΔMGMT and pSV2neo DNA were cotransfected into the packaging line GP+E86, followed by viral supernatant infection of the amphotropic cell line GP+envAm12 (Markowitz, D. et al. 1988) (Arthur Bank, Columbia University). To increase titer, a supernatant "ping-pong" method was used (Bodine et al. 1990).

Titer was estimated from supernatants collected after six daily media changes (Allay 1995) by infecting $1\times10^5$ K562 cells (as described below) with limiting dilutions of viral supernatant. The human chronic myelogenous leukemia cell line K562 was retrovirally transduced as described by Allay 1995. Briefly, wtMGMT and ΔMGMT producers were treated with 10 μg/ml mitomycin C and replated. Twenty-four hours later, K562 cells were added in the presence of human interleukin 3 (IL-3) (100 units/ml), human granulocyte-macrophage colony-stimulating factor (GM-CSF) (200 units/ml), and polybrene (8 μg/ml) and were collected after a 48-hour co-culture.

Post transduction cells were harvested and analyzed for colony-forming unit (CFU) (CFU-granulocyte-macrophage (GM), BFU-E (erythroid), and CFU-granulocyte erythroid macrophage megakaryocyte (CFU-GEMM) transduction efficiency, cell expansion, AGT expression and CFU drug resistance to compare gene transfer into CD34+ cells in the presence of hMSCs, Dexter stroma, FN and no stroma.

Transduction efficiencies for retroviral supernatant infection of human CD34+ cells in the presence of various human stroma conditions are shown in the Tables. These conditions were allogeneic (allo) or autologous (auto) MSCs (experiments 15-22 and 33-34, respectively), Dexter culture cells (experiments 26-32), fibronectin fragment CH 296 (FN) (experiments 23-25) or no stromal conditions (experiments 5-14).

CD34+ cells ($1-5\times10^5$ cells/ml) were transduced in the presence of human mesenchymal stem cells (allogeneic or autologous), Dexter stroma or fibronectin fragment CH-296 (FN), described above. Control plates were coated with BSA only. Cultures were supplemented with protamine sulfate (4 μg/ml), IL-3, IL-6 (both @ 20 ng/ml; Systemix, Palo Alto, Calif.), Flt-3 ligand (100 ng/ml; Immunex) and SCF (100 ng/ml; Amgen) or LIF (100 ng/ml; Systemix).

Cell expansion After a transduction period of 48-96 hours, a cell expansion (non-adherent cell count; see Reese et al. 1996, p. 14090) was obtained as follows: in the presence of autologous hMSCs, a cell expansion of about 2.4-fold (n=2); in the presence of allogeneic hMSCs a cell expansion of about 2.8±1.8 (n=7) was obtained; compared to 2.1 fold±0.5 (n=6) with Dexter stroma, 1.4 fold±0.1 (n=2) with FN, and 2.0±1.3 (n=10) in cultures without stroma (Table 1, column 6). Thus, culture expansion was not dependent on the presence of stroma or the type.

Transduction efficiency PCR was used to detect proviral specific sequences. To obtain genomic DNA for PCR analysis, individual colonies were resuspended in 30 ul of $H_2O$ and boiled for 6 minutes. One μl of proteinase K solution 10 mg/ml was added and the colonies were incubated at 55° C. for 2 hours and boiled again for 6 minutes. Six μl of each preparation was used per PCR reaction. Using sense primer 5'-TGGTACCTCACCCTTACCGAGTC-3' (SEQ ID NO:1) containing sequences of the MFG proviral backbone, and the antisense primer 5'-ACACCTGTCTGGTGAACGAAC-GACTCT-3' (SEQ ID NO:2) specific to human MGMT (Reese et al. 1996), transduction efficiency was determined. The transduction efficiency of allogeneic hMSCs was 51±15.5; Dexter stroma, 50±11 (N=6); and FN, 63 (n=1), compared to 40%±13 (n=10) in the absence of stroma (see Table 1, column 5).

Clonogenic efficiency The mean clonogenic efficiency of total mononuclear cells at the end of the culture was assayed as described in Allay et al. 1996. vM5MGMT-transduced $CD34^+$ cells ($3\times10^5$) were mixed with methylcellulose (Stem Cell Technologies, Vancouver, British Columbia, Canada), 100 ng/ml stem cell factor (Amgen, Thousand Oaks, Calif.), 100 units/ml IL-3 (Systemix, Palo Alto, Calif.), 2 units/ml erythropoietin (Amgen, Thousand Oaks, Calif.), 100 units/ml GM-CSF (Immunex, Seattle, Wash.) and 0.1 mM hemin (Sigma, St. Louis, Mo.), and plated in triplicate at 37° C. and 5% $CO_2$. After 12 days, colonies greater than 50 cells were enumerated. The results were similar for all conditions tested, 4.5%±1.7; n=31, indicating that clonogenic efficiency was independent of stromal type, expansion and transduction efficiency (Table 1, column 4).

FACS analysis for AGT expression ΔAGT was analyzed by flow cytometry as described in Liu et al. 1998, with modifications. Briefly, after cells were stabilized for 30 minutes using 1% paraformaldehyde, the membranes were permeabilized by incubating in 1% Tween 20 for 30 minutes at 37° C., (and omitted 30 minute incubation in 2% BSA/PBS). Non-specific binding sites were blocked for 30 minutes at 22° C. with 10% normal goat serum. Human AGT antibody mT3.1 (7 μg/ml) was added, and cells were incubated at 4° C. overnight. Cells were washed twice with 2% BSA/PBS and incubated with secondary antibody (goat anti-mouse IgG-1 (gamma) phycoerythrin conjugated) for 1 hour at 4° C. After washed as above, cells were resuspended in PBS+BSA for FACS analysis. Flow cytometry was performed using FACscan (Becton Dickinson, Mountain View, Calif.), equipped with an argon laser. MFI of permeabilized cells was determined by subtracting the nonspecific background (isotype control) from the fluorescence intensity of cells stained with specific AGT antibody (mT3.1) (provided by Drs. D. Bigner, Duke University and T. Brent, St. Jude Children's Research Hospital). Light scatter was used for gating on permeabilized cells. ΔAGT was expressed in 35% (n=2) of hematopoietic cells cultured with autologous and allogeneic hMSCs compared to 18.5% (n=2) for Dexter stroma and 65% (n=1) for FN (see Table 1 column 7).

Drug resistance conferred by ΔMGMT To evaluate drug resistance conferred by ΔMGMT, primary CFU survival at the TMZ or BCNU $IC_{50}$ and IC90 in transduced or untransduced cells was compared. IC50 (or IC90) is the determination of CFU survival after exposure to TMZ or BCNU in the presence of the AGT inhibitor BG. Following a retroviral transduction period of 72-96 hours, hematopoietic CD34+ progenitor cells were pretreated for 1 hour with 10 μM BG followed by increasing concentrations of TMZ or BCNU for 2 hours. Cells were washed free of drug, plated in methylcellulose and 5 μM BG was added to maintain depletion of endogenous AGT. After culture in methylcellulose, the colonies formed were counted as either CFU-GM, BFU-E and CFU-GEMM (referred to as CFU). Individual CFU were collected from 10 independent experiments, each from a different donor. Clonogenic ΔMGMT transduced cells had an average fold increase in the TMZ IC50 after exposure to BG of 5.2 (n=4) for allo MSC and auto MSC; 7.7 (n=2) for FN (see Table 2, col. 6). There was an increase in the TMZ IC90 after exposure to BG of >9.8 fold (n=4) for allo MSC and auto MSC; and >8.2 fold (n=2) for FN (see Table 2, col. 9).

Figure 1B:
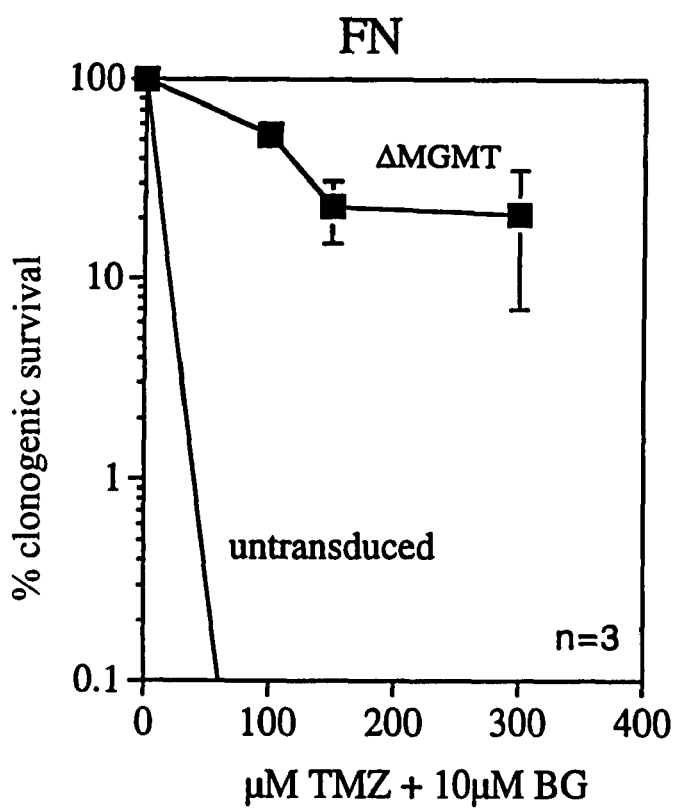
Figure 1C:
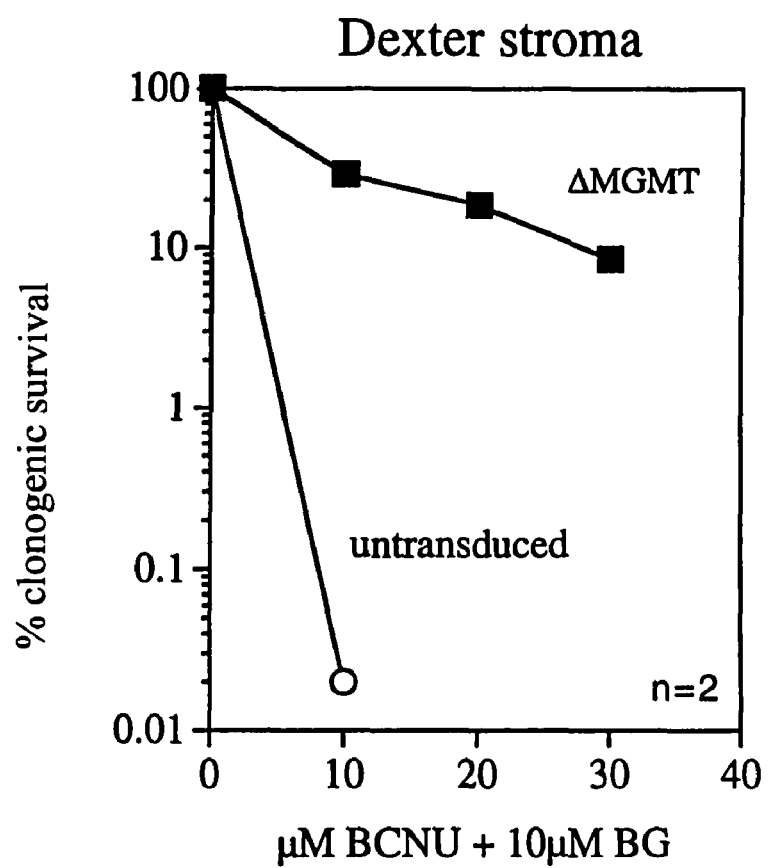
Figure 2A:
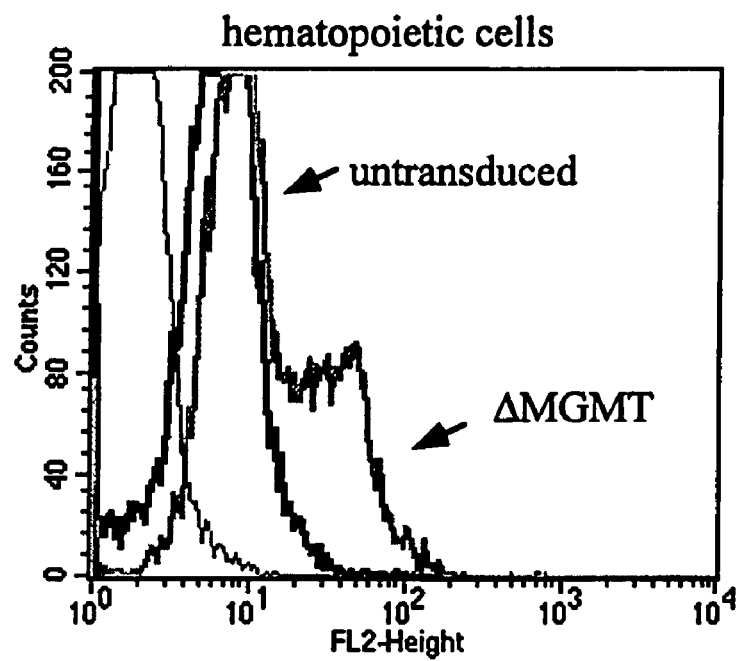
FIG. 2A-2B: AGT expression in simultaneously transduced hMSCs and CD34+ cells. CD34+ cells and hMSCs were cultured in the presence of retroviral supernatant for 72 hours. CD34+ cells were plated for 5 hours to deplete adherent cells while hMSCs were trypsinized and further cultured for 1 week with media changes. AGT expression was determined in both cell types by flow cytometry using the monoclonal antibody mT3.1. Shown is the percent AGT expression in transduced cells versus nontransduced cells in hematopoietic cells (FIG. 2A) and hMSCs (FIG. 2B).
Figure 2B:
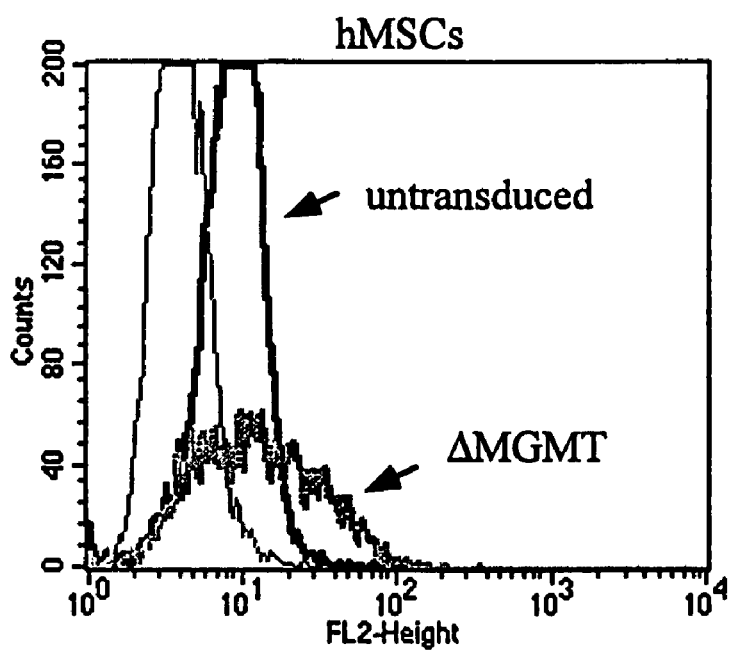

Clonogenic ΔMGMT transduced cells had an average increase in the BCNU IC50 after exposure to BG of 2 fold (n=1) for allo MSC; 2.8 fold (n=1) for FN and 5.6 fold (n=2) for Dexter (see Table 2, col. 6). There was an increase in the BCNU IC90 after exposure to BG of >6 fold (n=1) for allo MSC; >10 fold (n=1) for FN and 2.5 fold for Dexter (see Table 2, col. 9). Resistance of transduced cells compared to untransduced cells after exposure to BG is shown in FIG. 1. The transduced cells and untransduced cells were cultured in the presence of MSCs (FIG. 1A), FN (FIG. 1B), and Dexter (FIG. 1C).

These results demonstrate that hMSCs are able to support ex vivo gene transfer into CD34 human hematopoietic progenitor cells that exhibit transduction efficiencies, cell expansion and drug resistance properties comparable to the levels produced in Dexter stroma and FN enhanced transduction.

TABLE 1

| Experiment | Stroma type | Cytokines present in medium | CFU Clonogenic efficiency | CFU transduction efficiency | Total cells fold expansion | Total cells % AGT expression by FACS analysis |
|---|---|---|---|---|---|---|
| 1 | None, -RV | 3, 6, S | 4.9 | | 3.3 | |
| 2 | Dexter, -RV | 3, 6, S | 6 | | 1.7 | |
| 3 | MSC, -RV | 3, 6, S | 5.9 | | 4.8 | |
| 4 | None, -RV | 3, 6, S | 4.5 | | 1.2 | |
| | | | 5.3 ± .74 | | 2.8 ± 1.6 | |
| 5 | None | 3, 6, S | 1.7 | 60 | 1.3 | |
| 6 | None | 3, 6, S | 5 | 25 | 1 | |
| 7 | None | 3, 6, L | 5.1 | 33 | .86 | |
| 8 | None | 3, 6, L | 2 | 40 | 1.8 | |
| 9 | None | 3, 6, F, S | 4 | 50 | 1.2 | |
| 10 | None | 3, 6, F, S | 4.3 | 42 | 4.3 | |
| 11 | None | 3, 6, F, L | 5 | 42 | 3.7 | |
| 12 | None | 3, 6, F, L | 3.5 | 20 | 1.1 | |
| 13 | None | 3, 6 | 5.1 | 33 | 3.7 | |
| 14 | None | 3, 6 | 3 | 60 | 1.1 | |
| | | | 3.9 ± 1.3 | 40 ± 13 | 2 ± 1.3 | |
| 15 | allo MSC | 3, 6, S | | | | |
| 16 | allo MSC | 3, 6, L | | | 1 | |
| 17 | allo MSC | 3, 6, F, S | 5 | 50 | 6.6 | |
| 18 | allo MSC | 3, 6, F, S | 4.5 | | 1.8 | |
| 19 | allo MSC | 3, 6, F, S | 5 | | 2.0 | |
| 20 | allo MSC | 3, 6, F, S | 5 | | 2.3 | 40 |
| 21 | allo MSC | 3, 6, F, L | 4.9 | 67 | 3.6 | |
| 22 | allo MSC | 3, 6 | 4.8 | 36 | 2.7 | |
| | | | 4.9 ± .19 | 51 ± 15.5 | 2.8 ± 1.8 | |
| 23 | FN | 3, 6, F, S | 8.0 | | | 65 |
| 24 | FN | 3, 6, F, S | 3.1 | | 1.4 | |
| 25 | FN | 3, 6, F, S | 6.7 | 63 | 1.3 | |
| | | | 5.9 ± 2.5 | | 1.4 ± .1 | |
| 26 | Dexter | 3, 6, S | 3 | 50 | 2.8 | |
| 27 | Dexter | 3, 6, L | 5 | 70 | 2.4 | |
| 28 | Dexter | 3, 6, F, S | 3.7 | 50 | 1.9 | |
| 29 | Dexter | 3, 6, F, S | 2.6 | | 2.3 | 12 |
| 30 | Dexter | 3, 6, F, S | 4.4 | 40 | | 25 |
| 31 | Dexter | 3, 6, F, L | 3 | 40 | 2.1 | |
| 32 | Dexter | 3, 6 | 5 | 50 | 1.2 | |
| | | | 3.8 ± 1 | 50 ± 11 | 2.1 ± .5 | |
| 33 | auto MSC | 3, 6, F, S | 2.9 | | 1.4 | |
| 34 | auto MSC | 3, 6, F, L | 7.9 | | 3.3 | 30 |
| | | | 5.3 ± 3.7 | | | 2.4 ± 1 |

3: IL-3
6: IL-6
S: Stem Cell Factor
L: LIF
F: Flt-3
-RV: no retrovirus
no data indicates not tested

TABLE 2

| Experiment | Stroma type | Drug | CFU IC50 untransduced | CFU IC50 ΔMGMT | fold increase in ΔMGMT/ untransduced CFU IC50 | CFU IC90 untransduced | CFU IC90 ΔMGMT | fold increase in ΔMGMT/ untransduced CFU IC90 |
|---|---|---|---|---|---|---|---|---|
| 18 | Allo MSC | TMZ | 25.5 | 71 | 2.8 | 48 | >300 | >6 |
| 19 | Allo MSC | TMZ | 25 | 60 | 2.4 | 75 | >400 | >5.3 |
| 20 | Allo MSC | BCNU | 2 | 11.2 | 5.6 | 5 | >30 | >6 |
| 21 | Allo MSC | | | | | | | |
| 22 | Allo MSC | | | | | | | |
| 23 | FN | BCNU | | | 2.8 | | | |
| 24 | FN | TMZ | 9.8 | 123 | 12.5 | 29 | >300 | >10.3 |
| 25 | FN | TMZ | 25.5 | 70 | 2.8 | 48 | >300 | >6 |
| 26 | Dexter | | | | | | | |
| 27 | Dexter | | | | | | | |
| 28 | Dexter | | | | | | | |
| 29 | Dexter | BCNU | 2 | 3.9 | 2 | 5 | 20 | 2.5 |
| 30 | Dexter | BCNU | | | 9.1 | | | |
| 31 | Dexter | | | | | | | |
| 32 | Dexter | | | | | | | |
| 33 | auto MSC | TMZ | 9.8 | 64 | 6.5 | 29 | >300 | >10.3 |
| 34 | auto MSC | TMZ | 6.3 | 56 | 8.9 | 18.8 | 331 | 17.7 | no data indicates not tested
ΔMGMT: transduced
IC50, IC90 untransduced cells indicate cells cultured in the presence of indicated stroma but not transduced with retrovirus, however treated to same conditions as cells which were transduced with retrovirus.

CITED LITERATURE

Allay, J., et al. *Blood* 85:3342-3351 (1995)
Allay, J., O. Koç, et al. "Retroviral mediated gene transduction of human alkyltransferase complementary cDNA confers nitrosourea resistance to human hematopoietic progenitors *Clinical Cancer Research* 2:1353-1359 (1996)
Bodine, D. M., et al., *Proc. Natl. Acad. Sci. USA* 87, 3738-3742 (1990)
Edgington, *Biotechnology,* 10:1099-1106 (1992)
Hanenberg, H. K. Hashino et al. Optimization of fibronectin assisted retroviral gene transfer into human CD34+ hematopoietic cells. *Human Gene Therapy* 8:2193-2206 (1997)
Haynesworth et al. *Bone* 13(1):81-88 (1992)
Markowitz, D. et al. *J. Virol.* 167:400-406 (1988)
McLachlin et al., Progress in Nucleic Acid Research and Molecular Biology, 38:91-135 (1990)
Moore K., Deisseroth A., Reading C., Williams D., Belmont J. Stromal support enhances cell-free retroviral vector transduction of human bone marrow long-term culture initiating cells. *Blood* 79:1393-1399 (1992).
Nolta J., Smogorzewska E., Kohn D. Analysis of optimal conditions for retroviral-mediated transduction of primitive human hematopoietic cells. *Blood* 86:101-110 (1995)
Reese J O Koç et al. Retroviral transduction of mutant methylguanine DNA methyltransferase gene into human CD34 cells confers resistance to 06-benzylgaunine plus 1,3-bis (2-chloroethyl)-1-nitrosurea. *Proc Natl Acad Sci USA* 93:14088-14093 (1996)
Reese J Davis B et al. Simultaneous protection of G156A MGMT transduced hematopoietic progenitors and sensitization of tumor cells using O6-benzylguanine and temozolomide. (Submitted 1998)

The invention claimed is:

1. A method for transforming hematopoietic progenitor cells to express a protein, comprising co-culturing human hematopoietic progenitor cells with a homogenous population of human mesenchymal stem cells that have been isolated, purified and then culturally expanded from human mesoderm tissue, and transforming the human hematopoietic progenitor cells with a polynucleotide comprising exogenous genetic material encoding a protein in the presence of the isolated, purified, and culturally expanded human mesenchymal stem cells, wherein said protein is expressed.

2. The method of claim 1, wherein the mesenchymal stem cells are autologous to the hematopoietic progenitor cells.

3. The method of claim 1, wherein the mesenchymal stem cells are allogeneic to the hematopoietic progenitor cells.

4. The method of claim 1 further comprising separating the transformed human progenitor cells from the mesenchymal stem cells.

5. The method of claim 1, the homogenous population of mesenchymal stem cells uniformly expressing SH2, SH3, and SH4 surface antigens, and lacking surface markers for T and B lymphocytes, macrophages, and endothelial cells.

* * * * *